(12) United States Patent
Tan et al.

(10) Patent No.: US 8,288,087 B2
(45) Date of Patent: Oct. 16, 2012

(54) USE OF MELANOMA INHIBITORY ACTIVITY (MIA) PROTEIN AS AN EARLY INDICATOR FOR THERAPEUTIC RESPONSE IN MELANOMA

(75) Inventors: Nguyen Tan, San Leandro, CA (US); Eleni Venetsanakos, Oakland, CA (US); Michel Faure, Oakland, CA (US); Carla Heise, Benicia, CA (US)

(73) Assignee: Novartis AG, Basel (CH)

( * ) Notice: Subject to any disclaimer, the term of this patent is extended or adjusted under 35 U.S.C. 154(b) by 56 days.

(21) Appl. No.: 12/375,074

(22) PCT Filed: Jul. 26, 2007

(86) PCT No.: PCT/US2007/016848
§ 371 (c)(1),
(2), (4) Date: May 18, 2009

(87) PCT Pub. No.: WO2008/013912
PCT Pub. Date: Jan. 31, 2008

(65) Prior Publication Data
US 2010/0009392 A1    Jan. 14, 2010

Related U.S. Application Data

(60) Provisional application No. 60/820,756, filed on Jul. 28, 2006.

(51) Int. Cl.
*G01N 33/48*    (2006.01)
*G01N 33/50*    (2006.01)
*G01N 33/53*    (2006.01)
*G01N 33/574*    (2006.01)

(52) U.S. Cl. .................. 435/4; 435/7.1; 436/64; 436/813
(58) Field of Classification Search .................. None
See application file for complete search history.

(56) References Cited

U.S. PATENT DOCUMENTS 4,725,538 A * 2/1988 Senger .......................... 435/7.23
5,910,424 A    6/1999 Dooley et al.

FOREIGN PATENT DOCUMENTS

WO    2007/009191    1/2007

OTHER PUBLICATIONS

Sierra and del Torre (Angew Chem, Int Ed, 2000, vol. 39, pp. 1539-1559).*
Jachimczak et al (International Journal of Cancer, vol. 113, pp. 88-92).*
Abstract of Flaherty et al (Journal of Clinical Oncology, 2004, vol. 22, suppl. S, p. 711-S).*
Hochberg et al (British Journal of Dermatology, 2002, vol. 146, pp. 244-249).*
Abstract of Lee et al (Current Opinion on Investigational Drugs, 2003, vol. 4, pp. 757-763).*
Bosserhoff A-K et al: "Melanoma-Ihibitng Activity, a Novel Serum Marker for Progression of Malignant Melanoma", Cancer Research, American Association for Cancer Research, Baltimore, MD, US, vol. 57, No. 15, Aug. 1, 1997 pp. 3149-3153.
Bosserhoff A K et al: "Elevated MIA serum levels are of relevance for management of metastasized malignant melanomas: results of a German multicenter study", The Journal of investigative Dermatology Feb. 2000, vol. 114, No. 2, Feb. 2000, pp. 395-396.
Deichmann M et al: "Are responses to therapy of metastasized malignant melanoma reflected by decreasing serum values of S100beta or melanoma inhibitory activity (MIA)?", Melanoma Research, vol. 11, No. 3, Jun. 2001, pp. 291-296.
Carlson J A et al: "Molecular diagnostics in melanoma", Journal of the American Academy of Dermatology, C.V. Mosby, St. Louis, MO, US, vol. 52, No. 5, May 2005, pp. 743-775.
Menezes et al. "CHIR-258: A Potent Inhibitor of FLT3 Kinase in Experimental Tumor Xenograft Models of Human Acute Myelogenous Leukemia," Clin Cancer Res, 11(14) pp. 5281-5291, (2005).
Wilhelm et al. "BAY 43/9006 Exhibits Broad Spectrum Oral Antitumor Activity and Targets the RAF/MEK/ERK Pathway and Receptor Tyrocine Kinases Involved in Tumor Progression and Angiogenesis," Cancer Research, vol. 64, pp. 7099-7109, (2004).
Venetsanakos et al. "CHIR-265, a novel inhibitor that targets B-Raf and VEGFR, shows efficacy in a broad range of preclinical models," Proc Amer Assoc Cancer Res, vol. 47, Abstract #4854, (2006).

* cited by examiner

*Primary Examiner* — Karen Canella
(74) *Attorney, Agent, or Firm* — Foley & Lardner LLP

(57) ABSTRACT

The present invention provides a method for determining a response of a mammalian subject having melanoma tumor cells to treatment with a melanoma inhibitory agent. In one aspect, the method comprises (a) determining a first concentration of melanoma inhibitory activity protein (MIA) in a first biological sample taken from the mammalian subject before treatment with the melanoma inhibitory agent; (b) determining a second concentration of MIA in a second biological sample from the mammalian subject taken after treatment with the melanoma inhibitory agent; and (c) comparing the first and second concentrations of MIA, wherein a decrease in the second concentration of MIA measured in the second biological sample as compared to the first concentration of MIA measured in the first biological sample indicates a positive response to the treatment with the melanoma inhibitory agent.

14 Claims, 10 Drawing Sheets

Alignment of MIA Sequences

```
                   1                                                                    70
hMIA      (1)  MARSLVCLGVIII-    SGPGVRGGPMPKLADRKLCADQECSHPI MA ALQDYM PDCRFITTHRGQVV
rhMIA     (1)  MAWSLVFLGVIVLI    SGPGVGGGPMPKLADRKLCADQECSYPI MAVALQDYM PDCRFITTHRGQVV
chimpMIA  (1)  MARSLVCIGVIIL  SAFSGPGVRGGPMPKLADRKLCADQECSHPI MAVALQDYM PDCRFITTHRGQVV
mMIA      (1)  MVWSPVLIC    -VLSVFSGPSRADRA PKLADWKLCADEECSHPISMAVALQDVVAPDCRFITYRGQVV
rMIA      (1)  MVCSPVLIG    IVILSVFSGLSRADRA PKLADRKLCADEECSHPISMAVALQDVVAPDCRFITYRGQVV
dMIA      (1)  MAGSPVFL I I  VILLSAFLAPSVGGRA PKLADR  DE   Y  ISMAVALQDVVAPDCRFITHRGQVV
bovMIA    (1)  MAWSLMFL  -VILESAFPGPSAGCRPMPKLADRKMCADEECSHPISVAVA QDYM DCRFITTHRGQVV
hamMIA    (1)  -----------------------------ADRKLCADQECSHPISMAVA QDYM DCRFITTHRGQVV
pfMIA     (1)  ----------------------------NPIMIAR QDYYPADCXFIP RQGQLI 71                                                                   132
hMIA     (71)  YVFSKLKGRGRTFW G VQGDYYGGDI AARLGYFPSSIVREDQTIKPGKVDVKT D WDFYCQ
rhMIA    (71)  Y  KLKGRGRLFWGGSVQGDYYGGDI   GYFPSS    EDQ   KGVDVKTDKWDFYCQ
chimpMIA (71)  YMFSKLKGRGR  WGGSVQGDYYGG   AR GYFPSS TV EDQ TRPGKVDVKTDKWDFYCQ
mMIA     (70)  YVFSKLKGRGR FWGGSVQG  QGVY GDIAARLGYFPSSIVREDLNSKPGKIDMI DQWDFYCQ
rMIA     (70)  YVFSKLKGRGRL WGGSVQG  QGDIA AHLGYFPSSIVREDLTLKPGKV M TDEWDFYCQ
dMIA     (71)  VFSKLKGRGRLFWGGSVQG  QGDI AARLGYFPSSVVREDQTIKPGK IDVK DKWDFYCQ
bovMIA   (70)  IFSKLKGPGRLFWGGSVQGDYYGGEGAAARLG FPSS VRE  LKPAKTDVKTDVKTDKWDFYCQ
hamMIA   (42)  VFSKLKGRGRLFWGGSVQ DYYGDLAARLGY FPSSTVRE  TLKPGHWDVKTDK----
pfMIA    (29)  YAML KG  SQFWAGSWQDSWGQQEARIGHFPSSIVEETHPLMAAQTEVKTSNDFYCX-
```

FIGURE 1A

Alignment of MIA sequences from primates:

```
            1                                                                        70
hMIA     (1) MARSLVALGVILLISAFSGPGVRGGPMPKLADRKLCADQECSHPISMAVALQDYMAPDCRFLTLHRGQVV
chimpMIA (1) MARSLVILGVILLISAFSGPGVRGGPMPKLADRKLCADQECSHPISMAVALQDYMAPDCRFLTLHRGQVV
rhMIA    (1) MAWSLVFLGVVLLLSAFSGPGVGGGPMPKLADRKLCADQECSYPISMAVALQDYMAPDCRFLTLHRGQVV 71                                                                       131
hMIA    (71) YVFSKLKGRGRLFWGGSVQGDYYGDLAARLGYFPSSIVREDQTLKPGKVDVDKWDFYCQ
chimpMIA(71) YVFSKLKGRGRLFWGGSVQGDYYGDLAARLGYFPSSIVREDQTLKPGKVDVDKWDFYCQ
rhMIA   (71) YVFSKLKGRGRLFWGGSVQGDYYGDLAARLGYFPSSIVREDQTLKPGKVDVDKWDFYCQ
```

FIGURE 1B

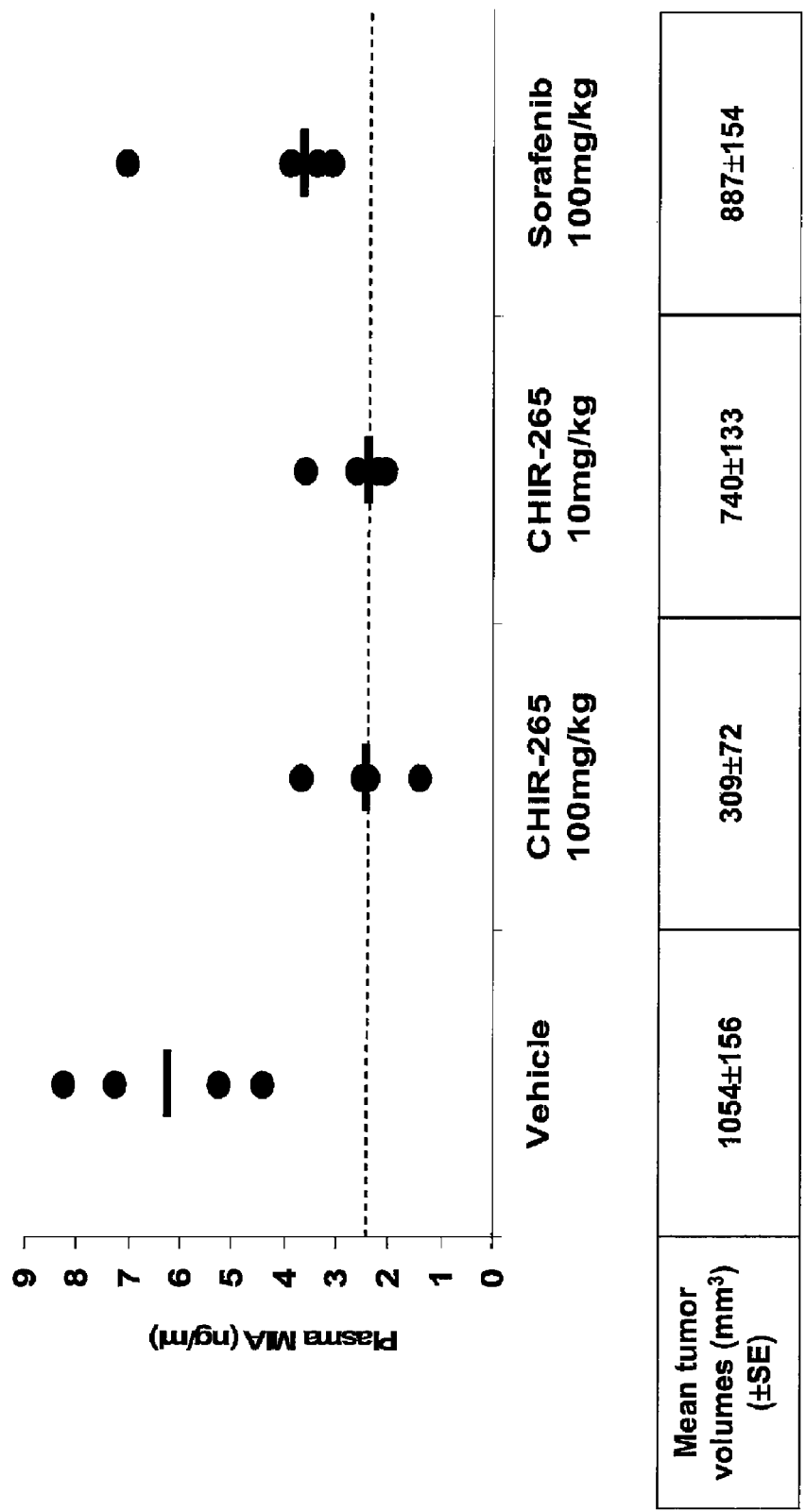

USE OF MELANOMA INHIBITORY ACTIVITY (MIA) PROTEIN AS AN EARLY INDICATOR FOR THERAPEUTIC RESPONSE IN MELANOMA

This application claims benefit of U.S. Provisional Application No. 60/820,756, filed Jul. 28, 2006, which in its entirety is herein incorporated by reference.

FIELD OF THE INVENTION

The present invention relates to the use of Melanoma Inhibitory Activity (MIA) Protein as an early indicator for response to treatment with a melanoma tumor cell inhibitor in mammalian subjects suffering from melanoma.

BACKGROUND OF THE INVENTION

Overall incidence rates for melanoma are increasing among men and women in the United States (see e.g., Edwards B. K. et al., *J. Nat. Cancer Inst.* 97:1407-1427 (2005)). Since 1981, the rate of increase has been about 3% per year. According to estimates from the American Cancer Society, there were about 59,580 new cases of melanoma in the U.S. in 2005, and about 7,700 people died of this disease (American Cancer Society Cancer Facts and Figures 2005, *Amer. Cancer Soc.* 2005:1-62). FDA approved treatments for metastatic melanoma include dacarbazine, interferon-alpha, and interleukin-2. However, the prognosis of patients with disseminated disease remains poor, with a 5-year survival rate of 16% or less in the U.S. Because of the limited efficacy of current treatments, the need for new therapies is particularly acute. New treatments such as anti-angiogenic agents, Raf kinase inhibitors and vaccines are currently being developed and may offer improvements in survival for patients with this disease (Mandara M. et al., *Expert Rev. Anticancer Ther.* 6:121-130 (2006)).

Given the high incidence of melanoma and limited efficacy of current treatments, a melanoma biomarker and assay for a melanoma biomarker is needed that could serve as an accurate early indicator for therapeutic response in a mammalian subject to measure the effectiveness of candidate melanoma inhibitory agents.

SUMMARY OF THE INVENTION

In accordance with the foregoing, in one aspect, a method is provided for determining a response of a mammalian subject having melanoma tumor cells to treatment with a melanoma inhibitory agent. The method comprises: (a) determining a first concentration of melanoma inhibitory activity protein (MIA) in a first biological sample taken from the mammalian subject prior to initiation of treatment with a melanoma inhibitory agent; (b) determining a second concentration of MIA in a second biological sample from the mammalian subject taken after initiation of treatment with the melanoma inhibitory agent; and (c) comparing the first and second concentrations of MIA, wherein a decrease in the second concentration of MIA measured in the second biological sample as compared to the first concentration of MIA measured in the first biological sample indicates a positive response to the treatment with the melanoma inhibitory agent.

In another aspect, the invention provides a method of evaluating the efficacy of a melanoma inhibitory agent for treating melanoma in a mammalian subject having melanoma. The method comprises (a) determining a first concentration of melanoma inhibitory activity protein (MIA) in a first biological sample taken from the mammalian subject prior to initiation of treatment with a melanoma inhibitory agent; (b) determining a second concentration of MIA in a second biological sample from the mammalian subject taken after initiation of treatment with the melanoma inhibitory agent; and (c) comparing the first and second concentrations of MIA, wherein a decrease in the second concentration of MIA measured in the second biological sample as compared to the first concentration of MIA measured in the first biological sample is indicative of the efficacy of the inhibitory agent for treating melanoma.

In another aspect, the invention provides a method of determining whether a patient should continue to receive treatment with a melanoma inhibitory agent. The method comprises (a) determining a first concentration of melanoma inhibitory activity protein (MIA) in a first biological sample taken from a mammalian subject prior to initiation of treatment with a melanoma inhibitory agent; (b) determining a second concentration of MIA in a second biological sample from the mammalian subject taken after initiation of treatment with the melanoma inhibitory agent; (c) comparing said first and second concentrations of MIA; and (d) determining that the patient should continue to be treated with the melanoma inhibitory agent if the second concentration of MIA is reduced by at least 20% in comparison to the first concentration of MIA.

In yet another aspect, the invention provides a method of identifying agents having utility in the treatment of melanoma. The method comprises (a) determining a first concentration of melanoma inhibitory activity protein (MIA) in a first sample taken from a cultured melanoma mammalian cell line before administering the agent to the melanoma mammalian cell line; (b) determining a second concentration of MIA in a second sample taken from the melanoma mammalian cell line after administrating the agent to the melanoma mammalian cell line; comparing the first and second concentrations of MIA; and (d) determining that the agent has utility in the treatment of melanoma if the second concentration of MIA is reduced by at least 20% in comparison to the first concentration of MIA.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A provides an amino acid sequence alignment of MIA protein isolated from various mammalian and non-mammalian species;

FIG. 1B provides an amino acid sequence alignment of MIA protein isolated from primates;

FIG. 4C graphically illustrates that MIA plasma levels decrease in response to tumor growth inhibition induced by oral dosing of CHIR-265 and Sorafenib in the MEXF 1341 human melanoma xenograft mouse model, as described in EXAMPLE 2;

DETAILED DESCRIPTION OF THE PREFERRED EMBODIMENT

Figure 2:
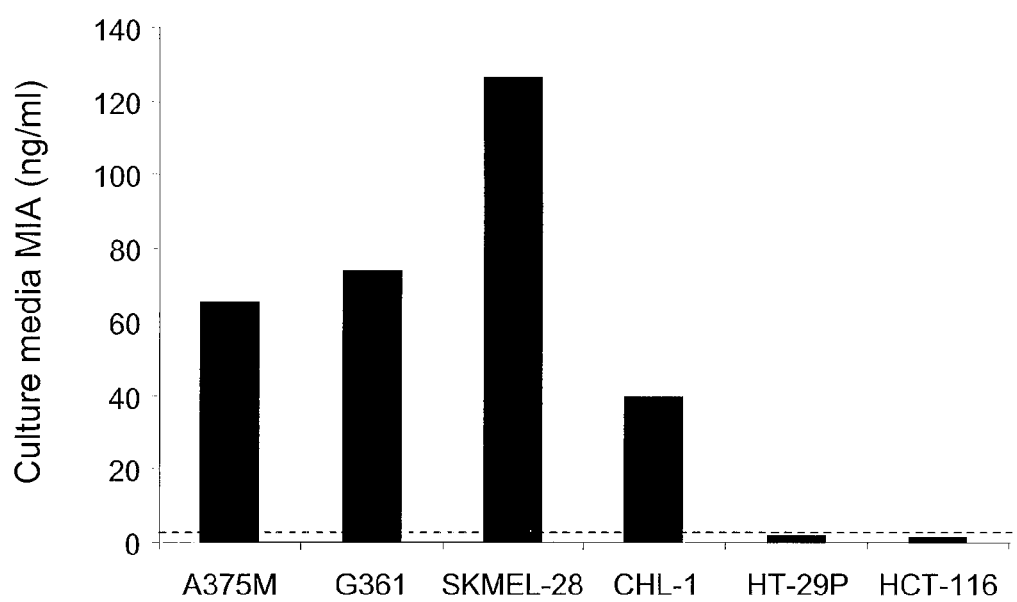
FIG. 2 graphically illustrates the results of an MIA ELISA assay demonstrating that MIA is secreted into culture media from melanoma cell lines, but not colon carcinoma cell lines, as described in EXAMPLE 1.

Unless specifically defined herein, all terms used herein have the same meaning as they would to one skilled in the art of the present invention. The following definitions are provided in order to provide clarity with respect to the terms as they are used in the specification and claims to describe the present invention.

As used herein, the term "positive response to the treatment in the mammalian subject" refers to a reduction in tumor volume and/or inhibition of tumor growth after treatment with a melanoma inhibitory agent.

In one aspect, a method is provided for determining a response of a mammalian subject having melanoma tumor cells to treatment with a melanoma inhibitory agent. The method comprises: (a) determining a first concentration of melanoma inhibitory activity protein (MIA) in a first biological sample taken from the mammalian subject prior to initiation of treatment with a melanoma inhibitory agent; (b) determining a second concentration of MIA in a second biological sample from the mammalian subject taken after initiation of treatment with the melanoma inhibitory agent; and (c) comparing the first and second concentrations of MIA, wherein a decrease in the second concentration of MIA measured in the second biological sample as compared to the first concentration of MIA measured in the first biological sample indicates a positive response to the treatment with the melanoma inhibitory agent.

As used herein, the term "Melanoma inhibitory activity ("MIA")" refers to a 12-kDa soluble protein publically available in the GenBank database as under the accession number NP_006524, encoded by the cDNA listed under GenBank accession number NM_006533, and mammalian homologs or a fragment thereof comprising at least ten consecutive residues of the MIA protein. MIA has been shown to be involved in the detachment of melanoma cells from the extracellular matrix by binding to fibronectin and laminin molecules, thereby preventing cell-matrix interaction (Brockez L. et al., *Br. J. Dermatol.* 143:256-268 (2000)). MIA was originally isolated from the supernatant of the human HTZ-19 melanoma cell line (Bogdahn U. et al., *Cancer Res.* 49:5358-5363 (1989)). As shown in FIG. 1A, the human MIA protein is 131 amino acids, wherein the first 24 amino acids comprise a signal sequence that directs the secretion of MIA into the extracellular compartment. The mature, secreted human MIA is 107 amino acids.

As further shown in FIG. 1A, MIA protein homologs have been identified in various mammalian and non-mammalian species including for example, rat (r), mouse (m), Chimpanzee (chimp), Rhesus monkey (rh), dog (d), bovine (bov), hamster (ham) and Puffer fish (pf). The human MIA amino acid sequence is provided in Genbank Number NP_006524; mouse MIA protein is provided as Genbank Number NP_062267; rat MIA protein is provided as Genbank Number NP_110479, hamster MIA protein is provided as Genbank Number AAF76220, cow MIA protein is provided as Genbank Number NP_776361, Rhesus monkey MIA protein is provided as Genbank Number XP_001098600, dog MIA protein is provided as Genbank Number XP_541610, chimpanzee MIA protein is provided as Genbank Number XP_512675 and Puffer fish MIA protein is provided as Genbank Number AAL26991, as accessed on Jul. 20, 2006, each of which is incorporated by reference.

In one embodiment, MIA proteins useful in the practice of the present invention are at least 70% identical (e.g., at least 80% identical, or at least 90% identical, at least 95% identical, at least 99% identical) to the human MIA protein amino acid sequence as provided in Genbank Number NP_006524, shown in FIG. 1A, or a fragment thereof comprising at least ten consecutive residues of the MIA protein.

The term "percent identity" or "percent identical" when used in connection with the MIA protein is defined as the percentage of amino acid residues in a candidate protein sequence that are identical with a subject protein sequence, after aligning the candidate and subject sequences to achieve the maximum percent identity. For example, percentage identity between two protein sequences can be determined by pairwise comparison of the two sequences using the bl2seq interface at the website of the National Center for Biotechnology Information (NCBI), U.S. National Library of Medicine, 8600 Rockville Pike, Bethesda, Md. 20894, U.S.A. The bl2seq interface permits sequence alignment using the BLAST tool described by Tatiana A., et al., "Blast 2 Sequences—A New Tool for Comparing Protein and Nucleotide Sequences", *FEMS Microbiol Lett.* 174:247-250, 1999. The following alignment parameters are used: Matrix=BLOSUM62; Gap open penalty=11; Gap extension penalty=1; Gap x_dropff=50; Expect=10.0; Word size=3; and Filter=off.

FIG. 1A provides an amino acid sequence alignment of exemplary MIA homologs. The percent identities for the various homologs of MIA shown in FIG. 1A are provided below in TABLE 1. As shown in FIG. 1B, and TABLE 1 the primate MIA amino acid sequence is very highly conserved, with human and chimpanzee having an identical sequence.

TABLE 1

MIA Percent Identity

|  | hMIA | rhMIA | chimpMIA | mMIA | rMIA | dMIA | bovMIA | hamMIA | pfMIA |
|---|---|---|---|---|---|---|---|---|---|
| hMIA | 100 | 96 | 100 | 81 | 83 | 88 | 85 | 73 | 38 |
| rhMIA |  | 100 | 96 | 82 | 83 | 91 | 87 | 73 | 38 |
| chimpMIA |  |  | 100 | 81 | 83 | 88 | 85 | 73 | 38 |
| mMIA |  |  |  | 100 | 92 | 84 | 80 | 66 | 37 |
| rMIA |  |  |  |  | 100 | 85 | 81 | 69 | 37 |
| dMIA |  |  |  |  |  | 100 | 86 | 70 | 37 |
| bovMIA |  |  |  |  |  |  | 100 | 67 | 40 |
| hamMIA |  |  |  |  |  |  |  | 100 | 56 |
| pfMIA |  |  |  |  |  |  |  |  | 100 |

MIA is a secreted protein, and therefore it can be detected in accessible tissues, such as biological fluids including blood (including plasma and serum), urine, and tissue samples such as melanoma tumor biopsy samples. Therefore, the presence or concentration of MIA measured before and after treatment may be used to determine a mammalian subject's response to treatment with a melanoma inhibitory agent, as described in EXAMPLES 1-2 and shown in FIGS. 2-4. It has also been demonstrated that a decrease in the concentration of MIA measured after treatment with a candidate melanoma inhibitory agent, as compared to the concentration of MIA before treatment, serves as an early and accurate indicator of the efficacy of the agent for treating melanoma in a mammalian subject, as described in EXAMPLES 3-4 and shown in FIGS. 4-5B.

In accordance with the method of this aspect of the invention, a first biological sample is taken from a mammalian subject before initiation of treatment with a melanoma inhibitory agent and a second biological sample is taken from the mammalian subject at least one time after initiation of treatment with the melanoma inhibitory agent. In some embodiments, plural treated biological samples from the subject (e.g., a subject in a preclinical trial) are taken over periodic intervals of time after initiation of treatment with the melanoma inhibitory agent has commenced.

As used herein the term "treatment" refers to the administration of one or more melanoma inhibitory agent(s) for the alleviation of symptoms associated with melanoma, or halt of further progression or worsening of those symptoms, or prevention or prophylaxis of melanoma. For example, successful treatment may include an alleviation of symptoms or halting the progression of the disease, as measured by a reduction in the growth rate of a tumor, a halt in the growth of the tumor, a reduction in the size of a tumor, partial or complete remission of the melanoma, or increased survival rate or clinical benefit. The term "initiation of treatment" refers to the time point of beginning of administration of the melanoma inhibitory agent(s).

For example, biological samples may be taken from the treated subject daily after initiation of treatment, or on a periodic basis after initiation of treatment with the melanoma inhibitory agent has commenced for a period of at least 3 days up to at least 3 months or longer. In some embodiments, biological samples from the treated subject are taken prior to initiation of treatment and at least once within a period of 3 days to 3 months (such as within 1 week, within 2 weeks, within 1 month, within 2 months, or within 3 month) after treatment commences.

Treatment regimens for melanoma inhibitory agents as contemplated herein are well known to those skilled in the art. For example, without limitation, a melanoma inhibitory agent may be administered to a patient in need thereof daily for 7, 14, 21, or 28 days, followed by 7 or 14 days without administration of the compound. In some embodiments, the treatment cycle comprises administering the amount of a melanoma inhibitory agent daily for 7 days, followed by 7 days without administration of the compound. A treatment cycle may be repeated one or more times to provide a course of treatment. In addition, a melanoma inhibitory agent may be administered once, twice, three times, or four times daily during the administration phase of the treatment cycle. In other embodiments, the methods further comprise administering the amount of a melanoma inhibitory agent once, twice, three times, or four times daily or every other day during a course of treatment.

In some embodiments, the treatment regimens further include administering a melanoma inhibitory agent as part of a treatment cycle. A treatment cycle includes an administration phase during which a melanoma inhibitory agent is given to the subject on a regular basis and a holiday, during which the compound is not administered. For example, the treatment cycle may comprise administering the amount of a melanoma inhibitory agent daily for 7, 14, 21, or 28 days, followed by 7 or 14 days without administration of the agent. In some embodiments, the treatment cycle comprises administering the amount of a melanoma inhibitory agent daily for 7 days, followed by 7 days without administration of the agent. A treatment cycle may be repeated one or more times to provide a course of treatment. In addition, a melanoma inhibitory agent may be administered once, twice, three times, or four times daily during the administration phase of the treatment cycle. In other embodiments, the methods further comprise administering the amount of a melanoma inhibitory agent once, twice, three times, or four times daily or every other day during a course of treatment. A course of treatment refers to a time period during which the subject undergoes treatment for cancer by the present methods. Thus, a course of treatment may extend for one or more treatment cycles or refer to the time period during which the subject receives daily or intermittent doses of a melanoma inhibitory agent.

The biological sample may be a tissue sample, or a fluid sample from the mammalian subject, such as a blood or urine sample, or clinical sample such as a melanoma biopsy sample. In some embodiments, the biological sample is a blood sample. The blood sample may be any type of blood sample suitable for measuring the presence of concentration of MIA protein. For example, whole blood; plasma (e.g., separated by centrifugation); or serum from plasma (e.g., obtained by clotting or serum separator tubes) may be used in the practice of the method of the invention.

The methods of the invention may be practiced in any mammalian subject having melanoma tumor cells, such as humans, Rhesus monkeys, Chimpanzees, mice, rats, dogs, cows, rabbits, guinea pigs, hamsters, goats, sheep, or horses.

The presence or concentration of MIA protein a first biological sample taken from a mammalian subject may be determined using any assay capable of detecting and/or measuring the amount of MIA protein. For example, the presence or concentration of MIA protein may be determined using immunofluorescence staining, flow cytometry, mass spectrometry, immunocytochemistry, immunohistochemistry, immunoblotting, or ELISA. In one embodiment, MIA protein concentration is measured in a biological sample of a mammalian subject using an antibody that specifically binds to MIA, such as an ELISA assay or a Western blot. An exemplary ELISA assay for detecting MIA levels in blood samples is described in EXAMPLE 1.

In another embodiment, MIA protein concentration is measured in a biological sample using Western blot analysis, as described in EXAMPLE 1.

In another embodiment, MIA protein concentration is measured in a biological sample using immunohistochemistry procedures. For example, a biological sample such as paraffin embedded human melanoma cell pellets, melanoma xenograft and melanoma and normal skin tissues isolated from patients may be used to evaluate the level of MIA expression by means of immunohistochemistry. Such immunohistochemistry procedures may be carried out using methods known by those of skill in the art, for example, MIA detection may be accomplished on the Ventana Discovery Autostainer (Ventana Medical Systems, Inc., Tucson, Ariz.) using cell conditioning 1 standard protocol for antigen retrieval. Tissue sections are incubated with no heat for 30-120 minutes with antibodies to human MIA and preimmune IgG controls (Novartis AG, Emeryville, Calif.) at 1-20 μg/ml. Ventata Universal Secondary (Ventana Medical Systems, Inc.) is added to the tissue sections and incubated for 10-60 minutes, followed by Ventana DABMap (Ventana Medical Systems, Inc) for detection. Ventana Hematoxylin and Bluing Reagent (Ventana Medical Systems, Inc.) may be used as a counter stain. Sections are dehydrated in graded alcohols, cleared in xylene and cover-slipped using a synthetic mounting media.

In accordance with the method of this aspect of the invention, a decrease in a second concentration of MIA measured in a second biological sample taken from a subject after initiation of treatment with the melanoma inhibitory agent as compared to a first concentration of MIA measured in a first biological sample taken from the subject prior to initiation of treatment (or in comparison to a predetermined reference level), is indicative of a positive response in the subject to treatment with the inhibitory agent. As shown in EXAMPLES 3 and 4, a correlation has been observed between a statistically significant decrease in MIA concentration in a biological sample from a mammalian subject after treatment with a melanoma inhibitory agent and a corresponding decrease in the melanoma tumor burden in the mammalian subject as compared to a mammalian subject having melanoma tumor cells and not receiving treatment with the inhibitory agent.

In some embodiments of the method, a decrease in MIA concentration in a biological sample taken at an early time point after treatment with a melanoma inhibitory agent, such as from 3 to 8 days after treatment has commenced, is an early indicator (e.g., predictive) of a reduction in tumor burden in the treated mammalian subject. In some embodiments, the reduction in tumor burden is due to regression of tumor volume as compared to the tumor volume at the start of treatment, thereby indicating that the inhibitory agent is cytotoxic to melanoma cancer cells. In other embodiments, the reduction in tumor burden is due to inhibition of tumor growth as compared to a control mammalian subject that does not receive the melanoma inhibitory agent, thereby indicating that the inhibitory agent is cytostatic to melanoma cancer cells.

In some embodiments, a decrease in MIA level of at least 20% measured in a biological sample taken from the mammalian subject within 3 months after treatment in comparison to a biological sample taken from an untreated subject indicates a positive response to the melanoma inhibitory agent. In some embodiments, a decrease in MIA level of at least 20% measured in a biological sample taken from the mammalian subject within 3 days after treatment in comparison to a biological sample taken from an untreated subject indicates a positive response to the melanoma inhibitory agent.

The methods of this aspect of the invention may be practiced to determine a mammalian subject's response to treatment with any melanoma inhibitory agent, such as a small molecule, protein therapeutic, antibody, nucleic acid molecule. As used herein, a melanoma inhibitory agent is any agent that causes growth inhibition of melanoma cells, either in vitro in cultured cells and/or in vivo in a mammalian subject. Examples of melanoma inhibitory agents useful in the practice of the invention include, but are not limited to CHIR-265, sorafenib, CHIR-258, Dacarbazine (DTIC, DTIC-Dome®), Temozolomide (Temodar®), Carmustine (BCNU, BiCNU®), Lomustine (CeeNU®), IL-2 (Proleukin®), and Interferon alpha-2b (IntonA®)).

In one embodiment, the methods of the invention are used to determine a response of a mammalian subject having melanoma tumor cells to treatment with a melanoma inhibitory agent selected from the group consisting of CHIR-265, sorafenib and CHIR-258, as described in more detail in EXAMPLES 2-4.

CHIR-265, currently known as RFB-265, is the compound {1-Methyl-5-[2-(5-trifluoromethyl-1H-imidazol-2-yl)-pyridin-4-yloxy]-1H-benzoimidazol-2-yl}-(4-trifluoromethyl-phenyl)-amine having the structure:

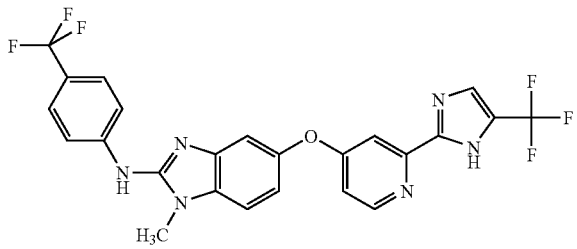

CHIR-265 is a novel Raf/VEGFR inhibitor as described in Venetsanakos E. et al., *Proc. Amer. Assoc. Cancer Res.* 2006: 47: Abstract 4854; Amiri P. et al., *Proc. Amer. Assoc. Cancer Res.* 2006:47: Abstract 4855; and Stuart D. et al., *Proc. Amer. Assoc. Cancer Res.* 2006:47: Abstract 4856, all of which are hereby incorporated by reference.

CHIR-258, currently known as TKI258, is the compound 4-amino-5-fluoro-3-[5-(4-methylpiperazin-1-yl)-1H-benz-imidazol-2-yl]quinolin-2(1H)-one, as described in U.S. Pat. No. 6,774,237. CHIR-258 is a multi-targeted RTK inhibitor as described in Lopes de Menezes D E et al., *Clin. Cancer Res.* 2005:11: 5281-5291 and Lee S H et al., *Clin. Cancer Res.* 2005:11:3633-3641, all of which are hereby incorporated by reference. Sorafenib (also known as "BAY 43-9006") is a Raf and Receptor Tyrosine Kinase (RTK) inhibitor as described in Wilhelm S. M. et al., *Cancer Res.* 64:7099-7109 (2004), incorporated herein by reference.

Figure 5A:
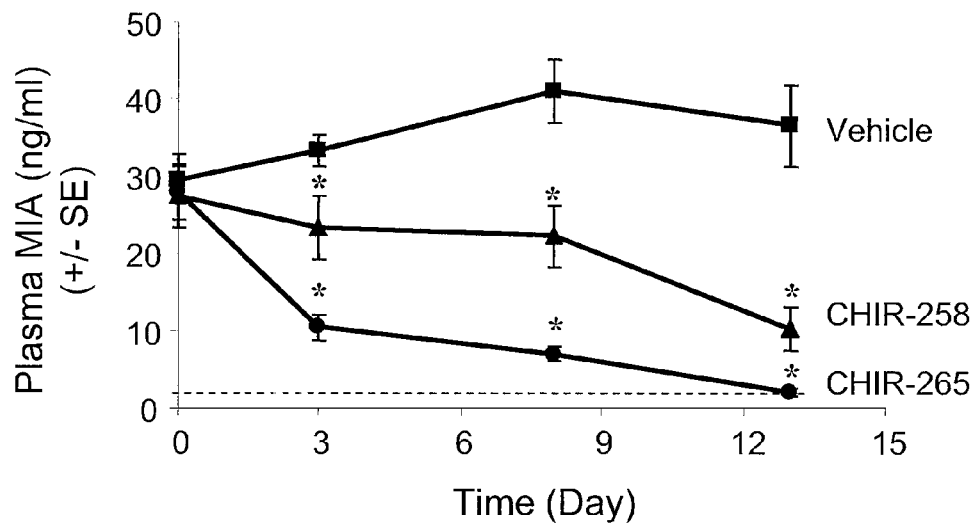
FIG. 5A graphically illustrates the early changes in MIA plasma levels in response to treatment with CHIR-258 and CHIR-265 in the A375M human melanoma xenograft mouse model, as described in EXAMPLE 3.

In one embodiment, the methods of the invention are used to determine a response of a mammalian subject having melanoma tumor cells to treatment with CHIR-265. In accordance with this embodiment, it has been observed that MIA levels rapidly decreased in biological samples obtained from melanoma tumor bearing animals orally dosed with CHIR-265 at 100 mg/kg every other day. As shown in FIG. 5A and described in EXAMPLE 3, MIA levels (starting at a median level of 27.8 ng/ml) decreased by day 3 in animals treated with CHIR-265 (100 mg/kg) to a median level of 10.4 ng/ml (a 62% reduction) which was associated with 29% tumor regression as measured on day 3 (see FIG. 5B).

Figure 4A:
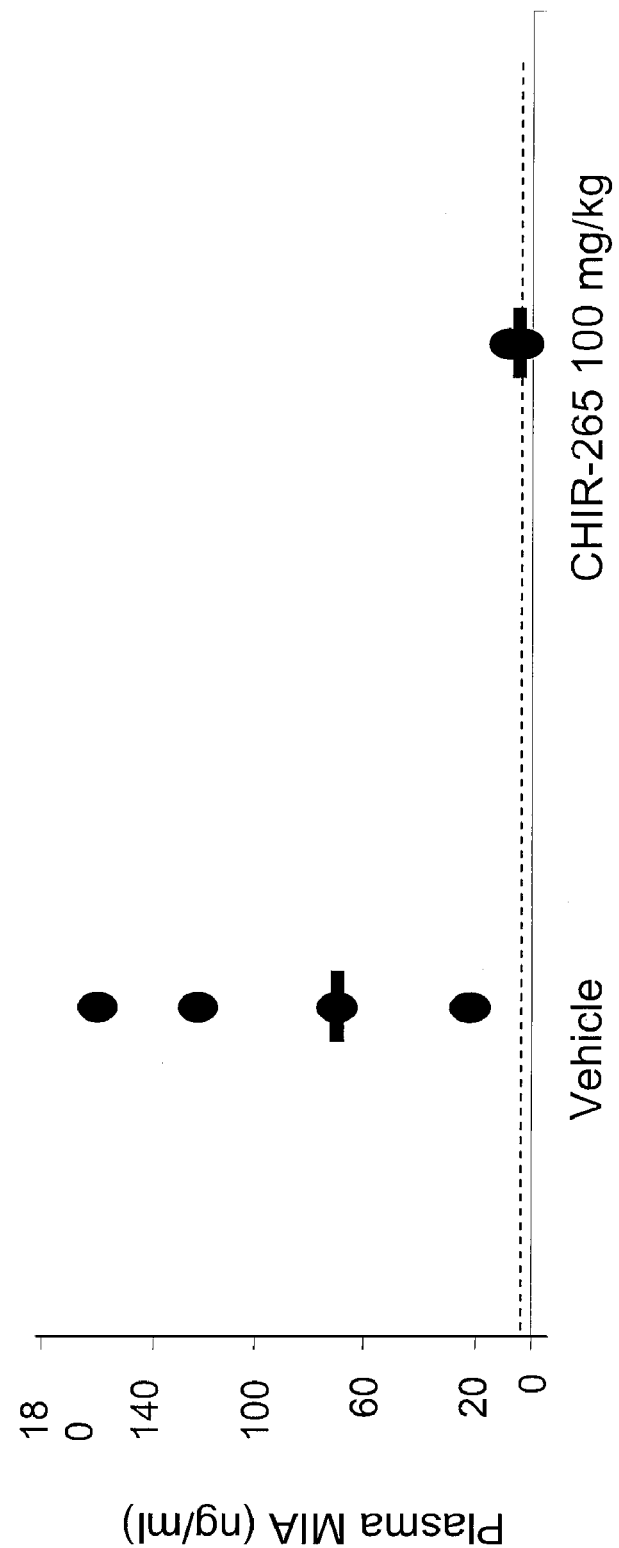
FIG. 4A graphically illustrates that MIA plasma levels decrease in response to tumor growth inhibition induced by oral dosing of CHIR-265 in the A375M human melanoma xenograft mouse model, as described in EXAMPLE 2.

In another embodiment, the methods of the invention are used to determine a response of a mammalian subject having melanoma tumor cells to treatment with CHIR-258. In accordance with this embodiment, it has been observed that MIA levels decreased in biological samples obtained from melanoma tumor bearing animals orally dosed with CHIR-258 at 60 mg/kg with 10 doses over a 13-day period. As shown in FIG. 4A, a statistically significant decrease in MIA was observed by day 3 in animals treated with CHIR-258 (60 mg/kg), which was associated with tumor growth inhibition as measured on day 8 (see FIG. 5B).

In some embodiments, a decrease in MIA concentration in a second biological sample obtained from a human subject after treatment, such as blood serum, in comparison to the MIA concentration in a first biological sample obtained from the human subject prior to treatment is utilized as an early efficacy endpoint to predict the efficacy of a melanoma inhibitory agent in reducing tumor burden in subjects enrolled in a clinical trial.

The methods of the invention may be used to determine a response of a mammalian subject to treatment with a melanoma inhibitory agent administered via any suitable route of administration. The melanoma inhibitory agent may be administered in a pharmaceutical composition. Conventional methods, known to those of ordinary skill in the art of medicine, can be used to administer the pharmaceutical composition to the mammalian subject via conventional routes (e.g., oral, subcutaneous, intrapulmonary, transmucosal, intraperitoneal, intrauterine, sublingual, intrathecal or intramuscular routes) by standard methods. For example, a melanoma inhibitory agent may be combined or administered with a pharmaceutically acceptable carrier, vehicle or diluent, which may take a wide variety of forms depending on the form of preparation desired for administration. For example, in preparing the compositions in oral dosage form, any of the usual pharmaceutical media may be employed, such as, for example, water, glycols, oils, alcohols, and the like.

The methods of the invention may be used to determine an effective amount of a melanoma inhibitory agent to administer to a mammalian subject. An effective amount means an amount or dose generally sufficient to bring about the desired therapeutic benefit in mammalian subjects undergoing treatment. Effective amounts or doses of a melanoma inhibitory agent may be determined by routine methods such as modeling, dose escalation studies or clinical trials, and by taking into consideration the routine factors, such as the mode or route of administration or drug delivery, the pharmacokinetics of the agent, the severity and course of the melanoma, the subject's previous or ongoing therapy, the subject's health status and response to drugs. An exemplary dose is in the range of from about 0.001 to about 200 mg per kg of subject's body weight per day, preferably about 0.05 to 100 mg/kg/day, or about 1 to 35 mg/kg/day. Alternatively, dosages may be administered on a periodic basis, such as once every other day (e.g., from 0.05 to 100 mg/kg every other day).

In another aspect, the invention provides a method of determining whether a mammalian subject should continue to receive treatment with a melanoma inhibitory agent. The methods of this aspect of the invention comprise (a) determining a first concentration of melanoma inhibitory activity protein (MIA) in a first biological sample taken from a mammalian subject prior to initiation of treatment with a melanoma inhibitory agent; (b) determining a second concentration of MIA in a second biological sample from the mammalian subject taken after imitation of treatment with the melanoma inhibitory agent; (c) comparing said first and second concentrations of MIA; and (d) determining that the patient should continue to be treated with the melanoma inhibitory agent if the second concentration of MIA is reduced by at least 20% in comparison to the first concentration of MIA. The methods according to this aspect of the invention may be practiced using any melanoma inhibitory agent, including those described herein. In some embodiments, the second biological sample is taken from the subject prior to initiation of treatment and at least once within a period of 3 days to 3 months (such as within 1 week, within 2 weeks, within 1 month, within 2 months, or within 3 month) after treatment commences.

In another aspect, the invention provides a method of evaluating the efficacy of a melanoma inhibitory agent for treating melanoma in a mammalian subject having melanoma. The method comprises (a) determining a first concentration of melanoma inhibitory activity protein (MIA) in a first biological sample taken from the mammalian subject prior to initiation of treatment with a melanoma inhibitory agent; (b) determining a second concentration of MIA in a second biological sample from the mammalian subject taken after initiation of treatment with the melanoma inhibitory agent; and (c) comparing the first and second concentrations of MIA, wherein a decrease in the second concentration of MIA measured in the second biological sample as compared to the first concentration of MIA measured in the first biological sample is indicative of the efficacy of the inhibitory agent for treating melanoma.

In some embodiments, the method of this aspect of the invention further comprises measuring the volume of the at least one melanoma tumor in the mammalian subject prior to treatment with the inhibitory agent; and at least one time after administration of the inhibitory agent and comparing the tumor volume measurements taken prior to initiation of treatment and after treatment to determine if tumor volume has decreased. In some embodiments of this aspect of the invention, a decrease in the serum concentration of MIA at a time prior to the detection of a measurable decrease in tumor volume positively correlates with the efficacy of the inhibitory agent for the treatment of melanoma. For example, as described in EXAMPLE 3, it was observed in a melanoma xenograft mouse model that treatment with a melanoma inhibitory agent CHIR-258 (60 mg/kg) resulted in a statistically significant decrease in MIA plasma concentration by day 3, which preceded, and was predictive of, the detection of a statistically significant reduction in tumor burden as compared to vehicle treated subjects observed at day 8 (see FIGS. 5A and 5B). Moreover, the degree of tumor reduction resulting from treatment with different melanoma inhibitory agents correlated with MIA plasma levels, e.g., CHIR-265 treatment (MIA below level of detection at 3 ng/ml, >97% tumor growth inhibition); sorafenib treatment (MIA 28.9 ng/ml, 69% tumor growth inhibition).

Tumor volume in a mammalian subject may be measured using any art-recognized method. For example, caliper measurements may be used to estimate tumor volume using the formula: (a×b²)×0.5, where "a" is the largest diameter and "b" is the length perpendicular to the diameter, as described in Example 2. Other useful techniques to detect tumor shrinkage in mammalian subjects, such as humans include imaging techniques such as computed tomography (CT) scan, magnetic resonance imaging (MRI) scan. Tumor shrinkage in conjunction with imaging techniques is typically evaluated using the Response Evaluation Criteria In Solid Tumors (RECIST) criteria as described in Jour Natl. Cancer Instit. 92: 205-216 (2000), incorporated herein by reference. Other techniques may be used to evaluate tumor metabolic activity in vivo including positron emission tomography (PET), Fluorodeoxyglucose (FDG-PET), and DNA synthesis may be evaluated using Fluorodeoxythymidine (FLT-PET). For preclinical models, additional techniques may be used that involve the use of melanoma tumor cells genetically modified with marker genes such as the luciferase gene.

The methods of the invention may be used to evaluate the efficacy of one or more candidate melanoma inhibitory agents in an animal model, such as in a preclinical trial. For example, the practice of an embodiment of the method of the invention is described using a human melanoma xenograft tumor model in EXAMPLE 2 below.

In yet another aspect, the invention provides a method of identifying agents having utility in the treatment of melanoma. The method comprises (a) determining a first concentration of melanoma inhibitory activity protein (MIA) in a first sample taken from a cultured melanoma mammalian cell line before administering the agent to the melanoma mammalian cell line; (b) determining a second concentration of MIA in a second sample taken from the melanoma mammalian cell line after administrating the agent to the melanoma mammalian cell line; (c) comparing the first and second concentrations of MIA; and (d) determining that the agent has utility in the treatment of melanoma if the second concentration of MIA is reduced by at least 20% in comparison to the first concentration of MIA.

The methods of this aspect of the invention may be practiced using any type of agent that is a candidate melanoma inhibitory agent for therapeutic use in the treatment of a mammalian subject suffering from melanoma. For example, the agent may be a small molecule, protein therapeutic, antibody, or nucleic acid molecule. In some embodiments, the methods are practiced to identify one or more agents from a plurality of agents, such as a combinatorial library of small molecules. The agent may be administered to the cultured melanoma mammalian cell in any manner suitable to the type of agent, using methods well known to those of skill in the art. In some embodiments, the methods may be practiced with a positive control melanoma inhibitory agent, such as CHIR-265, sorafenib or CHIR-258, as described herein. The methods may be practiced using any melanoma mammalian cell line, such as, for example, a human melanoma mammalian cell line selected from the group consisting of G361, SKMEL-28, A375M and CHL-1, as further described in EXAMPLE 1.

While the preferred embodiment of the invention has been illustrated and described, it will be appreciated that various changes can be made therein without departing from the spirit and scope of the invention.

EXAMPLE 1

This Example demonstrates that MIA is expressed in and secreted from human melanoma cell lines and is not expressed in human colorectal cancer cell lines.

Methods:

Cell lines: The human melanoma cell lines, G361, SKMEL-28 and CHL-1; and colon carcinoma cell line, HCT-116, were obtained from the American Type Culture Collection (ATCC) (Manassas, Va.). The human melanoma cell line A375M and the human colon carcinoma cell line HT-29P were obtained from the University of Texas, M. D. Anderson Cancer Center (Houston, Tex.).

Cell Culture: The G361, A375M and HT-29P cell lines were cultured in McCoy's 5A medium; the SKMEL-28 cell line was maintained in Minimum Essential Medium (MEM); the CHL-1 cell line was grown in Dulbecco's Modification of Eagle's Medium (DMEM); and the HCT-116 cell line was cultured in RPMI 1640 medium. All cell culture media was supplemented with 10% fetal bovine serum, 2 mM L-glutamine, 1 mM sodium pyruvate, 1× MEM vitamins, 1× MEM amino acids and 1× MEM non-essential amino acids. All cell lines were maintained at 37° C. in a 5% $CO_2$ humidified atmosphere.

Western Blot Analysis: Human melanoma cell lines (A375M, G361, SKMEL-28 and CHL-1) and human colon carcinoma cell lines (HT-29P and HCT-116) were washed twice in phosphate buffered saline (PBS, Mediatech, Inc., Herndon, Va.) and lysed in RIPA buffer (50 mM Tris HCl, pH 7.4, 150 mM NaCl, 1 mM EDTA, 1 mM EGTA, 2 mM sodium orthovanadate, 20 mM pyrophosphate, 1% Triton X-100, 1% sodium deoxycholate and 0.1% SDS), containing fresh 1 mM phenylmethylsulfonylfluoride, Complete Mini Protease Inhibitor Cocktail tablet (2 tablets/25 ml of lysis buffer) (Roche Diagnostics GmbH, Mannheim, Germany) and 1× Phosphatase Inhibitor Cocktail II (Sigma-Aldrich, St. Louis, Mo.), for 20 minutes on ice. Lysates were collected in centrifuge tubes, spun at 14K RPM at 4° C. for 20 minutes and filtered through QIAshredder tubes (QIAGEN, Inc., Valencia, Calif.). Protein concentrations were determined using the BCA assay according to the manufacturer's protocol (Pierce, Rockford, Ill.). Samples were processed for Western Blot by standard methods using Novex® 18% Tris-Glycine gel (Invitrogen, Carlsbad, Calif.). MIA was detected with a goat polyclonal antibody (R&D Systems, Minneapolis, Minn.), diluted 1:1000 in TBST (Tris buffer saline containing 0.1% Tween®20, Fisher Scientific, Hampton, N.H.) containing 5% dry milk and incubated overnight at 4° C. The secondary antibody was a horseradish peroxidase-linked anti-goat antibody (Vector Laboratories, Burlingame, Calif.) diluted 1:5000. Protein bands were visualized using Enhanced Chemiluminescence (Amersham Biosciences, Piscataway, N.J.). Equal loading and transfer were confirmed by β-actin detection (Sigma-Aldrich, St. Louis, Mo.). Human recombinant MIA proteins (MW 12-kDa) from two commercial sources were used as positive control (Axxora, LLC, San Diego, Calif. and ProSpec-Tany TechnoGene, LTD, Rehovot, Israel).

MIA ELISA Assay: Equal numbers of human melanoma and colorectal carcinoma cells (~250,000 cells for each cell line) were seeded onto tissue culture plates and the culture medium for each cell line was collected 48 hr later. Levels of MIA in culture media or plasma were measured by a commercial single-step ELISA kit according to the manufacturer's protocol (Roche Diagnostics Corporation, Indianapolis, Ind.). MIA concentrations in test samples were calculated using a standard curve ranging from 3-37 ng/ml. When the MIA concentration exceeded the highest standard concentration, the samples were diluted 1:5 and assayed again to have the results fall within the linear range of the standard curve. Data were evaluated using the Student t-test (two-tailed distribution, two-sample unequal variance), using $P \leq 0.05$ as the level of significance.

Results: Detectable levels of MIA protein were observed in a Western blot for all the human melanoma cell lines tested (A375M, G361, SKMEL-28 and CHL-1) and not in human colon carcinoma (HT-29P and HCT-116) cell lines (data not shown). The MIA protein observed in the melanoma cell lines co-migrated with the positive control recombinant MIA protein (MW 12 kDa). Equal loading and transfer on the Western blot was confirmed by β-actin detection (Sigma-Aldrich, St. Louis, Mo.).

FIG. 2 shows the results of the ELISA assay measuring MIA secretion into the culture media from the melanoma and colon carcinoma cell lines. As shown in FIG. 2, MIA secretion was detected in melanoma cell lines A375M, G361 SKMEL-28 and CHL-1 but was not detected in the colon carcinoma cell lines HT-29P and HCT-116. The dashed line ( - - - - ) indicates the detection limit of the assay (3 ng/ml).

These results demonstrate that MIA is expressed and secreted by melanoma cells lines and not by colon carcinoma cell lines.

EXAMPLE 2

This Example demonstrates that MIA may be used as a surrogate marker for tumor burden in human melanoma tumor-bearing mice.

Figure 3:
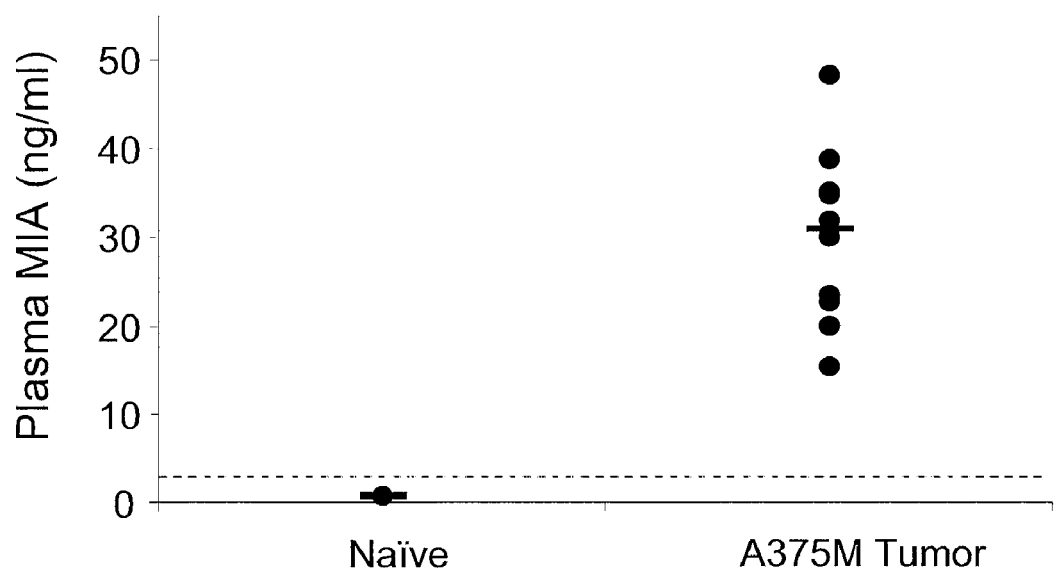
FIG. 3 graphically illustrates the results of an MIA ELISA assay on naïve non-tumor bearing mice (n=4) and athymic nude mice implanted with A375M human melanoma cells, having tumors approximately 250 mm$^3$ in volume (n=10), as described in EXAMPLE 2.

Methods:

Animal Models:

An A375 human melanoma xenograft study was carried out with female athymic nu/nu mice (8-12 weeks old) purchased from Charles River Laboratories (Wilmington, Mass.). Approximately $2.5 \times 10^6$ cells were implanted subcutaneously (s.c.) into the hind flank region of mice. Plasma samples were collected when tumors reached an average size of 250 mm$^3$ (n=10) and stored at −80° C. prior to MIA analysis. Dosing typically began when tumors reached an average size of 250 mm$^3$. Plasma samples from non-tumor-bearing (naïve) mice (n=4) were also collected for comparison, as shown in FIG. 3. Caliper measurements were performed twice weekly to estimate tumor volume using the formula: $(a \times b^2) \times 0.5$, where "a" is the largest diameter and "b" is the length perpendicular to the diameter.

An MEXF 276 human melanoma tumor explant xenograft study and an MEXF1341 human melanoma tumor explant xenograft study were carried out as follows. The MEXF 276 human melanoma tumor cells and the MEXF1341 human melanoma tumor explant cells were originally derived from surgical specimens isolated from different melanoma patients (obtained from Oncotest GmbH, Institute for Experimental Oncology, Frieburg, Germany) and propagated as xenografts in nude mice. After removal of tumors from donor mice, samples were cut into fragments (1-2 mm diameter) and placed in RPMI 1640 medium before subcutaneous implantation into recipient male NMRI nu/nu mice (6-8 weeks old). Dosing typically began when tumors reached an average size of 6-8 mm in diameter. Animals were maintained under cleanroom conditions in sterile filter-top cages and received sterile rodent chow and water ad libitum.

Therapeutic Agents: Small molecule compounds CHIR-265, sorafenib and CHIR-258 were synthesized at Chiron Corporation (Emeryville, Calif.). CHIR-265 and sorafenib were formulated in PEG400 buffer; CHIR-258 was dissolved in water. CHIR-265 is a novel Raf/VEGFR inhibitor (see Venetsanakos E. et al., *Proc. Amer. Assoc. Cancer Res.* 2006: 47: Abstract 4854; Amiri P. et al., *Proc. Amer. Assoc. Cancer Res.* 2006:47: Abstract 4855; and Stuart D. et al., *Proc. Amer. Assoc. Cancer Res.* 2006:47: Abstract 4856). CHIR-258 is a multi-targeted RTK inhibitor (see Lopes de Menezes D E et al., *Clin. Cancer Res.* 2005:11: 5281-5291; Lee S H et al., *Clin. Cancer Res.* 2005:11:3633-3641). Sorafenib is a Raf and Receptor Tyrosine Kinase (RTK) inhibitor (see Wilhelm S. M. et al., *Cancer Res.* 64:7099-7109 (2004)).

Treatment with Therapeutic Agents:

In a first experiment, A375M human melanoma tumor-bearing mice (n=5) were randomized and dosed orally with CHIR-265 at 100 mg/kg (n=5) or vehicle (n=5) once every other day. Tumor-bearing animals treated with PEG400 buffer alone were used as vehicle control. The percentage of tumor growth inhibition (TGI) after drug treatment was calculated as $100 \times [1-(\text{mean tumor volume}_{drug-treated}/\text{mean tumor volume}_{vehicle-treated})]$. Plasma samples were collected 48 hours post the fourth dose (day 10) for MIA analysis by ELISA. The results of the MIA ELISA assays are shown in FIG. 4A.

Figure 4B:
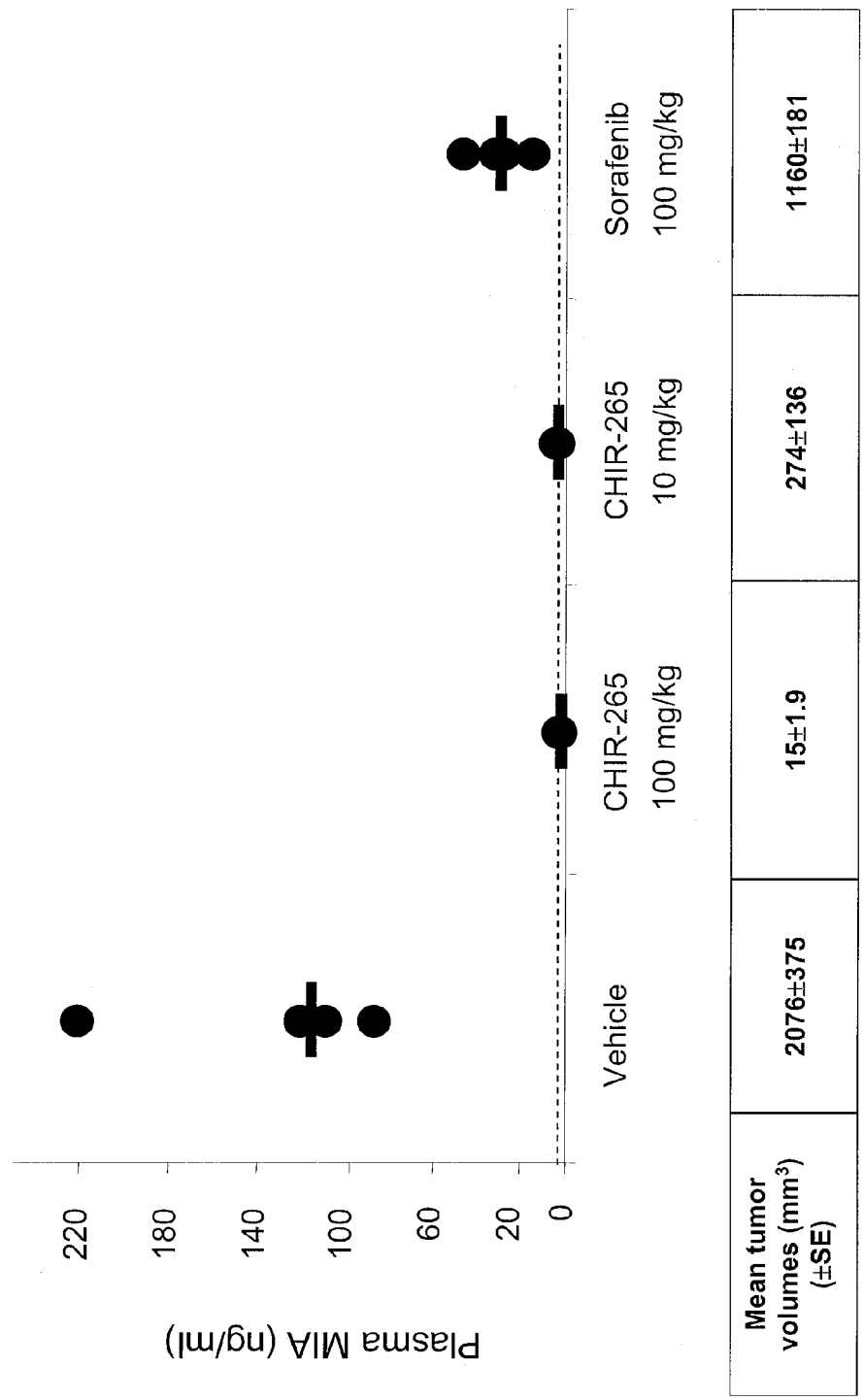
FIG. 4B graphically illustrates that MIA plasma levels decrease in response to tumor growth inhibition induced by oral dosing of CHIR-265 and Sorafenib in the MEXF 276 human melanoma xenograft mouse model, as described in EXAMPLE 2.

In a second experiment, MEXF 276 human melanoma tumor-bearing mice were randomized and dosed orally with CHIR-265 (100 or 10 mg/kg) or sorafenib (100 mg/kg) n=4/group. The first day of dosing was designated as Day 0. As such, the dosing schedule for CHIR-265 was 10 mg/kg on Day 0, 2, 4, 6, 14, 16 and 20. For CHIR-265 the dosing schedule was 100 mg/kg on Day 0, 2, 14, 16 and 20. Finally, the dosing schedule for sorafenib and PEG400 vehicle was 100 mg/kg every day on Day 0-20. Tumor volumes were measured twice per week and the percentage of tumor growth inhibition was determined as described above. The tumor volume measurements are shown in TABLE 2. Plasma samples were collected 4 hr after the last dose on Day 20 and stored at −80° C. prior to MIA analysis. MIA plasma levels were determined by an ELISA assay carried out as described in EXAMPLE 1. The results of the MIA ELISA assays are shown in FIG. 4B.

In a third experiment, MEXF 1341 human melanoma tumor-bearing mice were randomized and dosed orally with CHIR-265 (100 or 10 mg/kg) or sorafenib (100 mg/kg) n=4/group. The first day of dosing was designated as Day 0. As such, the dosing schedule for CHIR-265 (10 mg/kg) was 10 mg/kg on Day 0, 2, 4, 6, 14, 16 and 20. For CHIR-265 (100 mg/kg) the dosing schedule was 100 mg/kg on Day 0, 2, 14, 16 and 20. Finally, the dosing schedule for sorafenib and PEG400 vehicle was 100 mg/kg every day on Day 0-20. Tumor volumes were measured twice per week and the percentage of tumor growth inhibition was determined as described above. The tumor volume measurements are shown in TABLE 2. Plasma samples were collected 4 hr after the last dose on Day 20 and stored at −80° C. prior to MIA analysis. MIA plasma levels were determined by an ELISA assay carried out as described in EXAMPLE 1. The results of the MIA ELISA assays are shown in FIG. 4C.

Results:

FIG. 3 shows the results of an MIA ELISA assay on naïve non-tumor bearing mice (n=4) and athymic nude mice implanted with A375M human melanoma cells, having tumors approximately 250 mm$^3$ in volume (n=10). As shown in FIG. 3, MIA plasma levels ranging from 16 to 48 ng/ml (median value=31 ng/ml) were detected in melanoma tumor-bearing mice. In contrast, values obtained from the MIA ELISA assay in naïve animals were below the detection limit of the assay (3 ng/ml as indicated by the dashed line in FIG. 3). These results demonstrate that MIA is secreted in vivo in mice bearing human melanoma cells and can be detected in plasma by ELISA.

TABLE 2

Tumor Volume after Treatment with Melanoma Tumor Inhibitors

| Mouse Xenograft Model | Vehicle | CHIR-265 (100 mg/kg) | CHIR-265 (10 mg/ml) | Sorafenib |
|---|---|---|---|---|
| A375M | day 10: 436 ± 69.5 | day 10: 133 ± 14.1 | nd | nd |
| MEXF 276 | day 20: 2902 ± 374 | day 20: 19 ± 2.9 | day 20: 58 ± 15.2 | day 20: 887 ± 196 |
| MEXF 1341 | day 20: 1895 ± 535 | day 20: 575 ± 214 | day 20: 1190 ± 291 | day 20: 1338 ± 264 |

FIG. 4A graphically illustrates that MIA plasma levels decrease in response to tumor growth inhibition induced by oral dosing of CHIR-265 in the A375M melanoma xenograft mouse model. Each point on the graph represents data from an individual animal. $P \leq 0.05$ for MIA plasma levels in a comparison of vehicle vs. CHIR-265 treatments as determined by Student's t-test. The dashed line of the graph indicates the detection limit of the assay (3 ng/ml). As shown above in TABLE 2, the mean tumor volumes on day 10 for vehicle and CHIR-265 treated groups were 436±69.5 and 133±14.1 mm$^3$, respectively (±SE) (P<0.02). Therefore, CHIR-265 dosed orally at 100 mg/kg every other day caused significant tumor regression by almost 50% after four doses as compared to initial tumor volume (250 mm$^3$). This corresponded to 70% tumor growth inhibition when compared to vehicle treatment (p<0.02). As shown in FIG. 4A, a significant decrease in MIA plasma levels was associated with this tumor regression. MIA levels in all drug treated animals were near the lower limit of detection (4 ng/ml) after four doses of CHIR-265. In contrast, vehicle treated mice had a median MIA concentration of 69.2 ng/ml (ranging from 21 ng/ml to 119 ng/ml) that was 17-fold higher than CHIR-265 treated mice (n=5/group) ($P \leq 0.05$).

FIG. 4B graphically illustrates that MIA plasma levels decrease in response to tumor growth inhibition induced by oral dosing of CHIR-265 and Sorafenib in the MEXF 276 melanoma xenograft mouse model. As shown above in TABLE 2, the mean tumor volumes measured on day 20 for vehicle (2902±374 mm$^3$), CHIR-265 at 100 mg/kg (19±2.9 mm$^3$), CHIR-265 at 10 mg/kg (58±15.2 mm$^3$) and Sorafenib (887±196 mm$^3$) (±SE) (P<0.007 for all drug treated groups v. vehicle group). Therefore, it was observed that CHIR-265 and Sorafenib treatments caused significant tumor growth inhibition in the MEXF 276 melanoma model with >97% tumor growth inhibition induced by CHIR-265 at both doses and 69% tumor growth inhibition with sorafenib treatment. As shown in FIG. 4B, these tumor inhibition responses were associated with a significant decrease in MIA plasma levels in the treated animals. The median plasma MIA concentrations from vehicle (113.5 ng/ml) in comparison to sorafenib treated groups (28.9 ng/ml). MIA plasma levels from CHIR-265 treated groups were below the limit of detection (P<0.04 for all drug treatments v. vehicle). In addition, the degree of tumor reduction resulting from the different treatments correlated with MIA plasma levels, e.g., CHIR-265 treatment (MIA not detected, >97% tumor growth inhibition); sorafenib treatment (MIA 28.9 ng/ml, 69% tumor growth inhibition).

FIG. 4C graphically illustrates that MIA plasma levels decrease in response to tumor growth inhibition induced by oral dosing of CHIR-265 and Sorafenib in the MEXF 1341 melanoma xenograft mouse model. As shown above in TABLE 2, the mean tumor volumes measured on day 20 for vehicle (1895±535 mm$^3$), CHIR-265 at 100 mg/kg (575±214 mm$^3$), CHIR-265 at 10 mg/kg (1190±291 mm$^3$) and Sorafenib (1338±264 mm$^3$) (±SE) (P>0.08 for all drug treated groups v. vehicle group). Therefore, it was observed that CHIR-265 and Sorafenib treatments did not cause significant tumor growth inhibition in the MEXF 276 melanoma model with 37% to 70% tumor growth inhibition induced by CHIR-265 at both doses. As shown in FIG. 4C, despite a lower level of basal plasma MIA in MEXF1341 xenografts as compared to MEXF276, a significant (2-fold) reduction in MIA was detected in response to both CHIR-265 treatments (P<0.02). Sorafenib treatment also reduced plasma MIA levels (P>0.17). Consistent with the results observed in the A375M and MEXF276 xenograft models, the degree of tumor reduction in the MEXF1341 xenograft model resulting from the different treatments correlated with plasma MIA levels. The results of the xenograft models MEXF276 and MEXF1341 are predictive for human tumors because the tumor cells were isolated from a human melanoma patient and serially passaged in nude mice. Because these tumor cells were not grown in culture, they more closely resemble the characteristics of the original tumor in the human subject.

These results indicate that MIA plasma levels serve as a sensitive surrogate marker for tumor burden and response to treatment with melanoma inhibitory agents in animals bearing melanoma tumors.

EXAMPLE 3

This Example demonstrates that MIA is a early and accurate indicator for anti-tumor drug activity in preclinical melanoma models.

Methods: The kinetics of MIA concentrations in plasma following drug treatment were investigated as follows. A375M tumor-bearing mice were dosed orally either with CHIR-265 (100 mg/kg), CHIR-258 (60 mg/kg) or vehicle (n=10/group). Plasma samples were collected before dosing was initiated, and again on day 3, 8 and 13. Tumor volumes were measured at the same time points, using methods described in EXAMPLE 2.

Results: FIG. 5A graphically illustrates the early and significant changes in MIA plasma levels in response to treatment with CHIR-258 and CHIR-265 in the A375M human melanoma xenograft model. *P<0.05 for all comparisons vs. vehicle. Error bars indicate standard errors (SE). The dashed line indicates the detection limit of the assay.

Figure 5B:
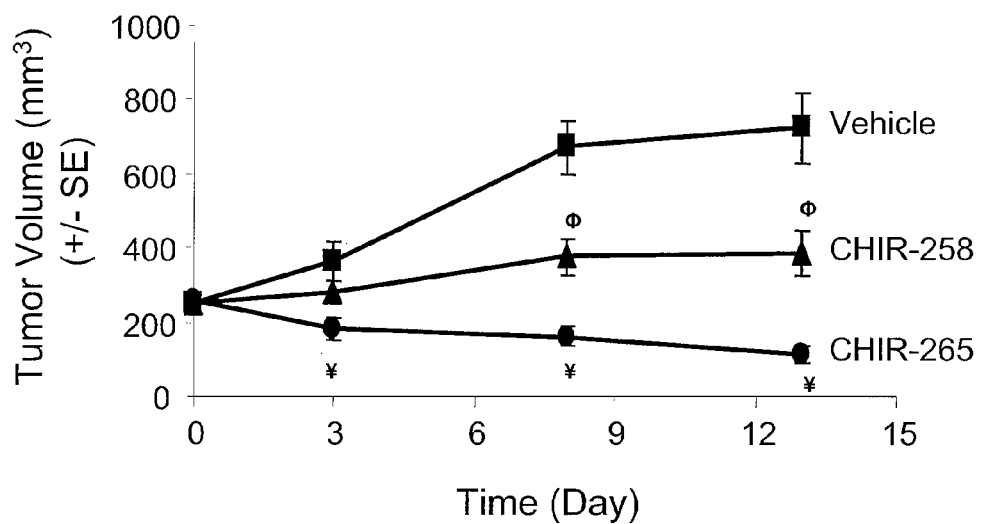
FIG. 5B shows the tumor volumes in the A375M human melanoma tumor bearing mice prior to dosing (day 0) and at days 3, 8 and 13 after treatment with CHIR-258 or CHIR-265 in comparison to vehicle controls, as described in EXAMPLE 3.

FIG. 5B shows the tumor volumes in the A375M human melanoma tumor bearing mice at day 3, 8 and 13 after treatment with CHIR-258 or CHIR-265 in comparison to vehicle controls. $^{¥}$P<0.01 for CHIR-265 vs. vehicle, $^{Φ}$P<0.005 for CHIR-258 vs. vehicle. Error bars indicate standard errors (SE).

The results in FIGS. 5A and 5B show that both CHIR-258 and CHIR-265 caused statistically significant decreases in MIA plasma concentration by day 3, which continued to decrease during treatment (P<0.05). The baseline MIA concentration measured at day 0 was 27.8 ng/kg. The reduction in MIA plasma concentration was more pronounced with treatment with CHIR-265, which induced tumor regression, as compared to CHIR-258 which resulted in tumor inhibition but not regression. After treatment with CHIR-265, MIA concentrations had decreased to 10.4 ng/ml by day 3, a 62% reduction in MIA concentration which was associated with 29% tumor regression (FIG. 5A). By day 13, MIA concentrations were undetectable in the CHIR-265 treated group. CHIR-258 treatment resulted in tumor growth inhibition, however regressions were not observed. Nevertheless, MIA levels were reduced by day 3 to statistically significant lower levels in comparison to vehicle and were reduced by 63% on day 13 compared to baseline.

These data demonstrate that MIA is an early indicator for drug activity and that changes detected by ELISA in circulating MIA levels precede observable volumetric changes in tumor burden. Treatment with the compounds CHIR-265 and CHIR-258 resulted in various degrees of tumor growth inhibition and/or tumor regression and concomitant with these effects on tumor burden, there was a significant and correlative decrease in MIA plasma levels. For example, CHIR-265 treatment induced tumor regression with a rapid and significant decrease in MIA levels, whereas CHIR-258 treatment resulted in tumor growth inhibition with a less dramatic reduction in MIA levels.

Another significant observation was that MIA levels decreased earlier and with greater amplitude than did the tumor volumes. This was exemplified by significant decreases in MIA levels at the early time points in the dosing schedules. Even when the tumor volume stabilized, as observed with CHIR-258 treatment, the MIA levels continued to decrease. While not wishing to be bound by theory, this effect may be attributed to the presence of necrotic and dying cells that contributed to tumor volume, but no longer secreted MIA.

Based on these preclinical results, clinical studies in humans may show decreased MIA levels before tumor response can be measured, thus providing an early indication that there is a positive response in the human subject in response to a melanoma inhibitory agent. Moreover, the data described herein suggest that MIA may be useful in human clinical trials of agents that are cytostatic as well as for agents that are cytotoxic.

EXAMPLE 4

This Example demonstrates that MIA may be used as a surrogate marker for tumor burden in CHL-1 human melanoma tumor-bearing mice.

Methods:
Animal Models:
A CHL-1 human melanoma xenograft study was carried out with female athymic nu/nu mice (8-12 weeks old) purchased from Charles River Laboratories (Wilmington, Mass.). Approximately $5 \times 10^6$ tumor cells in Matrigel™ were implanted subcutaneously (s.c.) into the hind flank region of mice. Dosing began when tumors reached an average size of 200 mm$^3$. Caliper measurements were performed twice weekly to estimate tumor volume using the formula: $(a \times b^2) \times 0.5$, where "a" is the largest diameter and "b" is the length perpendicular to the diameter.

Therapeutic Agents: Small molecule compound CHIR-258 was prepared as described in EXAMPLE 2.

Treatment with Therapeutic Agents: CHL-1 human melanoma tumor-bearing mice were randomized and dosed orally with CHIR-258 at 30 mg/kg and 80 mg/kg (n=10/group) once every day. The first day of dosing was designated as day 0. Plasma samples were collected prior to dosing, and on day 8 and day 22. A vehicle control group was also used in the study (n=10).

Figure 6A:
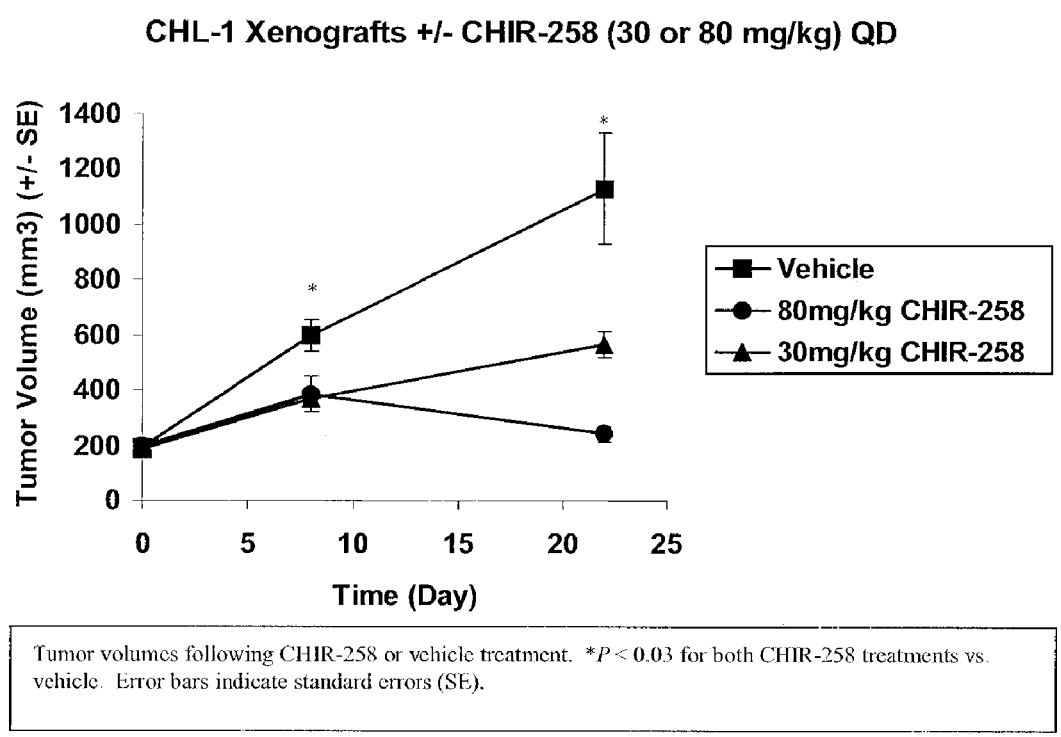
FIG. 6A shows the tumor volumes in the CHL-1 human melanoma tumor bearing mice prior to dosing (day 0) and at days 8 and 22 after treatment with CHIR-258 (at 30 mg/kg and 80 mg/kg) in comparison to vehicle controls, as described in EXAMPLE 4.

Results: FIG. 6A graphically illustrates tumor volume in CHL-1 human melanoma tumor cell bearing mice following treatment with CHIR-258 or vehicle control. *P<0.03 for both CHIR-258 treatments vs. vehicle. Error bars indicate standard errors (SE). As shown in FIG. 6A, CHIR-258 dosed at 30 mg/kg or 80 mg/kg once daily caused significant tumor growth inhibition (P<0.03) by day 8 as compared to vehicle treatment.

Figure 6B:
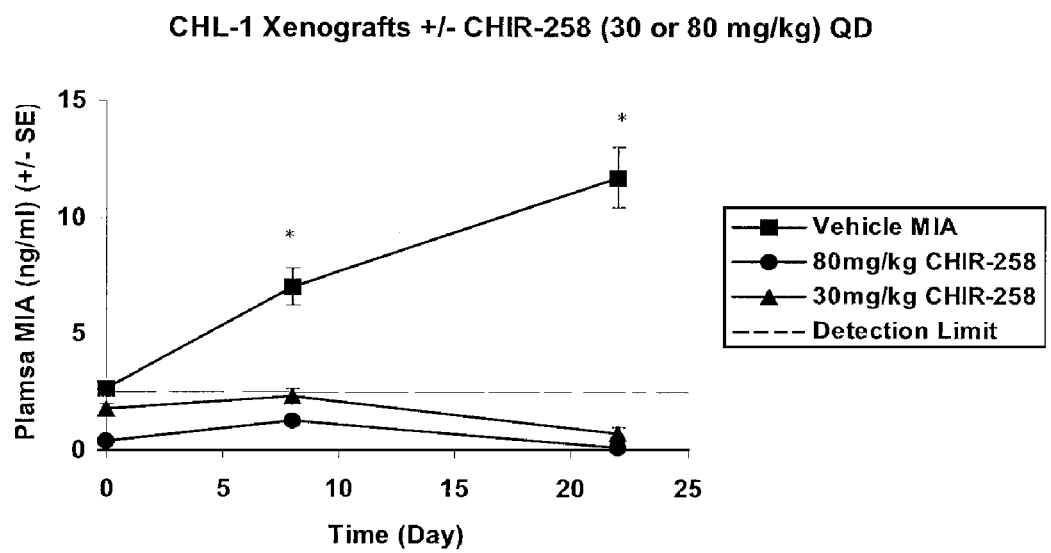
FIG. 6B graphically illustrates the early changes in MIA plasma levels in response to treatment with CHIR-258 (at 30 mg/kg and 80 mg/kg) in the CHL-1 human melanoma xenograft mouse model, as described in EXAMPLE 4.

FIG. 6B graphically illustrates the effect of CHIR-258 treatment on MIA plasma concentration. *P<0.05 for all comparisons vs. vehicle. Error bars indicate standard errors (SE). The dashed line indicates the detection limit of the assay. As shown in FIG. 6B, CHIR-258 significantly inhibited MIA secretion when administered at both the 30 mg/kg and 80 mg/kg dosages. As further shown in FIG. 6B, plasma MIA levels in all groups of mice prior to dosing was near or below the limit of detection of the assay. It is interesting to note that the MIA levels in CHL-1 xenografts prior to dosing (2.6 ng/ml) were lower than the MIA levels in A375M human melanoma xenograft mice (31 ng/ml as described in EXAMPLE 2), even through the average starting tumor volumes prior to dosing were in similar range (200 vs. 250 mm$^3$, respectively). The median plasma MIA level in the control group of the CHL-1 xenograft study was approximately 7.7 ng/ml by day 8, whereas plasma MIA levels from both groups treated with CHIR-258 were not detectable by day 8 and subsequent time points (see FIG. 6B).

These results suggest that although treatment with CHIR-258 caused tumor growth inhibition and not regression, the drug was effective at significantly reducing plasma MIA levels. These results are consistent with the findings in the A375M melanoma xenograft model, as described in EXAMPLE 2. While not wishing to be bound by theory, this effect may be attributed to the presence of necrotic and dying cells that contributed to tumor volume, but no longer secrete MIA. The results further support the use of MIA as an early indicator for drug response and efficacy in the treatment of melanoma.

While the preferred embodiment of the invention has been illustrated and described, it will be appreciated that various changes can be made therein without departing from the spirit and scope of the invention.

The invention claimed is:

1. A method for determining a response of a mammalian subject having human melanoma tumor cells to treatment with CHIR-265, comprising:
   (a) determining a first concentration of melanoma inhibitory activity protein (MIA) in a first biological sample comprising plasma, taken from the mammalian subject prior to initiation of treatment with CHIR-265;
   (b) selecting the mammalian subject having a first concentration of MIA of at least 16 ng/mL for treatment with CHIR-265;
   (c) determining a second concentration of MIA in a second biological sample comprising plasma, taken from the mammalian subject after initiation of treatment with CHIR-265; and
   (d) comparing the first and second concentrations of MIA, wherein a decrease in the second concentration of MIA measured in the second biological sample as compared to the first concentration of MIA measured in the first biological sample indicates a positive response to the treatment with CHIR-265.

2. The method of claim 1, wherein a decrease in the second concentration of MIA in the second biological sample measured within 3 months after initiation of treatment indicates a positive response to treatment with CHIR-265.

3. The method of claim 1, wherein a decrease in the second concentration of MIA in the second biological sample measured within one week after treatment indicates a positive response to treatment with CHIR-265.

4. The method of claim 1, wherein a decrease of at least 20% in the second concentration of MIA in the second biological sample as compared to the first concentration of MIA in the first biological sample indicates a positive response to treatment with CHIR-265.

5. The method of claim 1, wherein a decrease in the second concentration of MIA is used as an efficacy endpoint for evaluating the mammalian subject's response to treatment with CHIR-265.

6. A method of evaluating the efficacy of CHIR-265 for treating melanoma in a mammalian subject having melanoma comprising:
   (a) determining a first concentration of melanoma inhibitory activity protein (MIA) in a first biological sample comprising plasma, taken from the mammalian subject prior to initiation of treatment with CHIR-265;
   (b) selecting the mammalian subject having a first concentration of MIA of at least 16 ng/mL for treatment with CHIR-265;
   (c) determining a second concentration of MIA in a second biological sample comprising plasma, taken from the mammalian subject after initiation of treatment with CHIR-265; and
   (d) comparing the first and second concentrations of MIA, wherein a decrease in the second concentration of MIA measured in the second biological sample as compared to the first concentration of MIA measured in the first biological sample is indicative of the efficacy of CHIR-265 for treating melanoma.

7. The method of claim 6, wherein the second biological sample is taken within 3 months after initiation of treatment with CHIR-265.

8. The method of claim 6, wherein the second biological sample is taken within one week after initiation of treatment with CHIR-265.

9. A method of determining whether a mammalian subject should continue to receive treatment with a melanoma inhibitory agent, comprising
   (a) determining a first concentration of melanoma inhibitory activity protein (MIA) in a first biological sample comprising plasma, taken from the mammalian subject prior to initiation of treatment with CHIR-265;
   (b) selecting the mammalian subject having a first concentration of MIA of at least 16 ng/mL for treatment with CHIR-265;
   (c) determining a second concentration of MIA in a second biological sample comprising plasma, taken from the mammalian subject after initiation of treatment with CHIR-265;
   (d) comparing said first and second concentrations of MIA; and
   (e) determining that the mammalian subject should continue to be treated with CHIR-265 if the second concentration of MIA is reduced by at least 20% in comparison to the first concentration of MIA.

10. The method of claim 9, wherein the second biological sample is taken within 3 months after initiation of treatment with CHIR-265.

11. The method of claim 9, wherein the second biological sample is taken within one week after initiation of treatment with CHIR-265.

12. A method for determining a response of a mammalian subject having human melanoma tumor cells to treatment with CHIR-265, comprising:
   (a) determining a first concentration of melanoma inhibitory activity protein (MIA) in a first biological sample, taken from the mammalian subject prior to initiation of treatment with CHIR-265;
   (b) determining a second concentration of MIA in a second biological sample, taken from the mammalian subject after initiation of treatment with CHIR-265; and
   (c) comparing the first and second concentrations of MIA, wherein a decrease in the second concentration of MIA measured in the second biological sample as compared to the first concentration of MIA measured in the first biological sample indicates a positive response to the treatment with CHIR-265, and
wherein the positive response correlates to tumor size reduction.

13. The method of claim 12, wherein the second biological sample is taken within 3 months after initiation of treatment with CHIR-265.

14. The method of claim 12, wherein the second biological sample is taken within one week after initiation of treatment with CHIR-265.

* * * * *